US00PP13115P2

(12) United States Plant Patent
Winchel

(10) Patent No.: US PP13,115 P2
(45) Date of Patent: Oct. 22, 2002

(54) HYBRID TEA ROSE PLANT NAMED 'WEKPEARL'

(75) Inventor: Joseph F. Winchel, Long Beach, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/713,289

(22) Filed: Nov. 17, 2000

(51) Int. Cl.[7] ..... A01H 5/00
(52) U.S. Cl. ..... Plt./132
(58) Field of Search ..... Plt./132, 133, 130

*Primary Examiner*—Bruce R. Campell
*Assistant Examiner*—June Hwu
(74) *Attorney, Agent, or Firm*—Christie, Parker & Hale, LLP

(57) ABSTRACT

A new variety of Hybrid Tea rose suitable for garden decoration, having flowers of ivory coloration slightly washed with pink.

1 Drawing Sheet

GENUS AND SPECIES DESIGNATION

The genus and species of the new variety is *Rosa hybrida* cv. 'WEKpearl'.

BACKGROUND OF THE INVENTION

This invention relates to a new and distinct variety of Hybrid Tea Rose. The varietal denomination of the new variety is 'WEKpearl'. Its parentage is unknown because it was discovered as a seedling in a controlled planting of mixed rose varieties.

SUMMARY OF THE INVENTION

Among the features which distinguish the new variety from other presently available and commercial rose cultivars known to the inventor are the following combination of characteristics: its heavy caliper peduncle which is almost entirely smooth, its numerous prickles on the underside of the rachis and its dark gold filaments. The plant is an upright growing plant, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'WEKpearl' may be asexually propagated by cuttings, budding and grafting.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of 3 to 4 year-old rose plants of the new cultivar grown outdoors in Upland, Calif. in the month of October. Phenotypic expression may vary with environmental, cultural and climatic conditions, as well as differences in conditions of light and soil.

FLOWER

The new variety usually bears its flowers singly. Flowers are borne on strong long stems (about 29 to about 50 cms.). Outdoors the plant blooms very abundantly and nearly continuously during the growing season. The flowers have a slight tea fragrance. The flower receptacle is average to somewhat long length (about 1.4 to about 1.9 cm) and about 1.5 to about 2.0 cm in width at the widest point, very globular in form and between 138A and 144A in color when immature, sometimes lightly suffused on the side exposed to sun with between 183B and 183C. The flower receptacle surface is very smooth with some hairs and thick fleshy walls.

BUD

The peduncle is about 5.5 to about 11.5 cms. in length, of heavy caliper and usually erect. It is almost entirely smooth, with very few stipitate glands. Peduncle color is between 138A and 144A sometimes lightly suffused on the side exposed to sun with between 183B and 183C.

Before the calyx breaks, the bud is about 1.7 to 2 cms. in diameter at the widest point, about 2.5 to about 3 cms. in length and pointed to ovoid in shape. The surface of the bud bears some small slender foliaceous appendages and few stipitate glands usually with stout moderately cut foliaceous parts extending beyond the tip of the bud about ¾ or more of its length. Bud color is between 138A and 144A sometimes lightly suffused on the side exposed to sun with between 183B and 183C.

The inner surface of the sepals is covered with fine wooly tomentum; sepal margins are lined with some stipitate glands. The sepals are about 2.3 to about 3.5 cm in length and about 0.8 to about 1.2 cm in width at the widest point.

As the petals open (after the calyx breaks), the bud is about 2.2 to about 2.6 cms. in diameter at the widest point, about 2.9 to about 3.7 cms. in length, and very pointed to ovoid in form. The color of the under and upper surfaces of the newly opened petals is between 4D and 19D sometimes moderately blushed near the petal edge with as dark as between 60C and 61B. At the point where the petal attaches, there is a moderately small zone between 3C and 5C.

BLOOM

When fully open, the bloom ranges from about 9.5 to 12 cms. in diameter. Petalage is double with about 32 to 36 petals and about 5 to 7 petaloids arranged irregularly. When partially open, the bloom form is very high centered and the petals are spiraled to somewhat cupped with petal edges slightly reflexed outward. When fully open, the bloom form is more cupped and the petals are more flat to cupped with petal edges more reflexed to somewhat rolled outward.

PETALS

The substance of the petals is moderately heavy and of medium thickness with upper surfaces somewhat satiny and under surfaces more matte to shiny in finish. The outer petals are nearly round to broadly obovate in shape with rounded apices. The inner petals are more broadly obovate in shape with rounded apices.

NEWLY OPENED FLOWER

On the under surface of the outer petals, at the point where the petal attaches, there is a moderately small zone as deep as between 9C and 12B that gradually suffuses to between 4D and 159D. The petal edge is sometimes very lightly blushed with as dark as between 63B and 61C. On the upper surface of the outer petals, at the point where the petal attaches, there is a moderately large zone as deep as between 9B and 12A that gradually suffuses to between 4D and 159D. The petal edge is sometimes lightly blushed with as dark as between 63B and 61C.

The under and upper surfaces of the intermediate petals is similar in coloration to the under and upper surfaces of the outer petals but with much less evidence of the blush coloration.

The under and upper surfaces of the inner petals is similar in coloration to the under and upper surfaces of the outer petals but with no evidence of the blush coloration.

The general tonality of the newly opened flower is between 4D and 159D with a very light blush of as dark as between 63B and 61C on the outer petals edges.

THREE-DAY-OLD FLOWER

On the under surface of the outer petals, at the point where the petal attaches, there is a moderately small zone between 12D and 9D that gradually suffuses to lighter than between 8D and 159D. The petal edge is sometimes very lightly blushed with as dark as between 63C and 62A. On the upper surface of the outer petals, at the point where the petal attaches, there is a moderately large zone between 9D and 12C that gradually suffuses to lighter than between 8D and 159D. The petal edge is sometimes lightly blushed with as dark as between 63C and 62A.

The under and upper surfaces of the intermediate petals is similar in coloration to the under and upper surfaces of the outer petals but with much less evidence of the blush coloration.

The under and upper surfaces of the inner petals is similar in coloration to the under and upper surfaces of the outer petals but with no evidence of the blush coloration.

The general tonality of the newly opened flower is lighter than between 8D and 159D with a very light blush of between 63C and 62A on the outer petals edges.

On the spent bloom, the petals persist, fading to between 155D and 159D.

In October in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are many in number (average about 230) and are arranged regularly about the pistils; a few are mixed with petaloids. The filaments are irregular in length (about 0.9 to about 1.3 cm), most with anthers. Filaments are bewteen 9B and 13A in color. The anthers all open approximately at the same time. Anther color is between 21B and 22A when immature and between 165A and 200C at maturity. Pollen is abundant and between 22C and 23C in color.

FEMALE REPRODUCTIVE ORGANS

Pistils vary in number (average about 200). The styles are very uneven length (about 0.5 to about 0.8 cm) and moderately bunched. Stigma color is between 6C and 7C. Style color is between 2C and 3C sometimes slightly suffused close to the stigma with near 46C. Ovaries are usually all enclosed in the clayx.

Hips have not been noted on this variety when grown in Upland, Calif.

FOLIAGE

The compound leaves are usually comprised of three to five or more leaflets and are borne abundantly. The five-leaflet leaves are about 10.8 to 13.9 cms. in length and about 9.8 to 13.1 cms. in width at the widest point and are semi-glossy in finish. The terminal leaflets are about 5.6 to 8.1 cms. in length and about 3 to 4.8 cms. in width at the widest point, somewhat oval to ovate in shape with acuminate apices and round bases. Their margins are usually simply serrate.

The upper surface of the mature leaf is between 137A and 139A. The under surface of the mature leaf is between 138B and 139C. The upper surface of the young leaf is between 144A and 144B sometimes heavily suffused with between 187A and 183A. The under surface of the young leaf is of similar coloration to the upper surface but with heavier suffusion of the dark pigment.

The rachis is very rough. The upper side is grooved with some stipitate glands on the edges of the grooves. The under side of the rachis is very rough with some stipitate glands and many prickles of assorted sizes.

The stipules are about 1.0 to about 1.4 cms. in length and of medium width (about 0.4 to about 0.6 cm in width at the widest point) with straight points that usually turn out at an angle of more than 45 degrees.

The plant displays an average degree of resistance to powdery mildew and rust as compared to other commercial varieties grown under comparable conditions in Upland, Calif. As indicated by the USDA Plant Hardiness Zone Map, the plant's winter hardiness is bewteen zone 5b and 6a.

GROWTH

The plant has an upright medium growth habit (about 130 to 160 cms. in height and about 110 to 140 cms. spread at the widest point), with moderately branching. It displays moderately vigorous growth.

The color of the major stems is between 138B and 139C. They bear many large prickles that are about 0.6 to 1.1 cms. in length. The large prickles are hooked slightly downward with a moderately broad base; prickle color is between 165C and 166D. The major stems bear few small prickles of similar shape and coloration.

The color of the branches is between 146A and 137C. They bear many large prickles that are of similar size and shape to the large prickles on the major stems; prickle color is between 162B and 160A. The branches bear some small prickles of similar shape and coloration. The color of the new shoots is between 144B and 144A often heavily suffused with between 187B and 183A. They bear many large prickles which are of similar size and shape to the large prickles on the major stems; prickle color is between 144B and 144A usually heavily suffused with between 187B and 187A. The new shoots bear few small prickles of similar shape and coloration.

I claim:

1. A new and distinct Hybrid Tea rose plant of the variety substantially as described and illustrated herein.

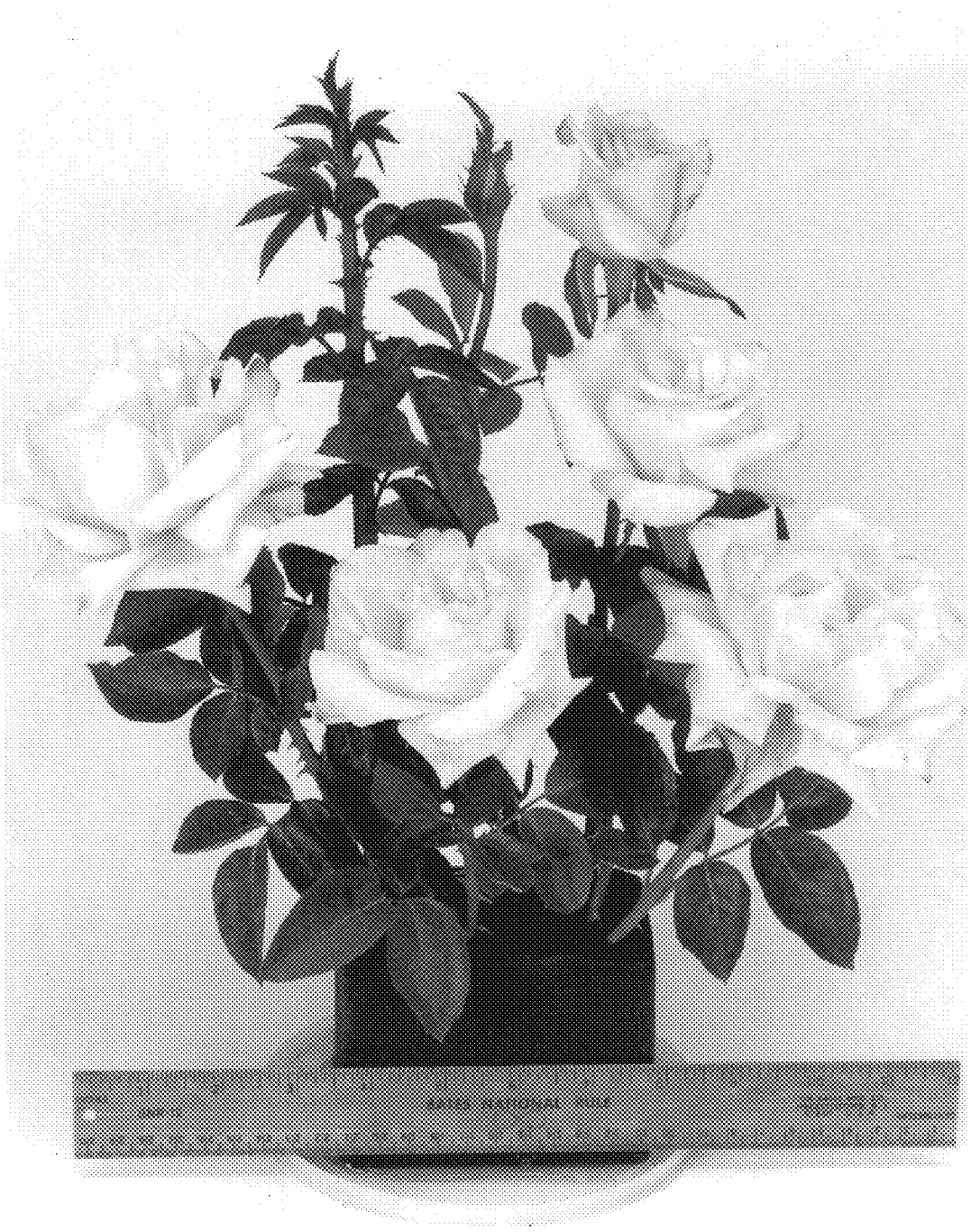

* * * * *